United States Patent [19]

Klainer et al.

[11] Patent Number: 5,094,958

[45] Date of Patent: Mar. 10, 1992

[54] METHOD OF SELF-COMPENSATING A FIBER OPTIC CHEMICAL SENSOR

[75] Inventors: Stanley M. Klainer; Kisholoy Goswami, both of Henderson, Nev.

[73] Assignee: FiberChem Inc., Las Vegas, Nev.

[21] Appl. No.: 575,165

[22] Filed: Aug. 30, 1990

[51] Int. Cl.$^5$ .............................................. G01N 21/76
[52] U.S. Cl. ..................................... 436/172; 356/408; 250/227.23; 250/458.1
[58] Field of Search ................. 436/166, 172, 805; 356/320, 408, 318, 250, 319; 250/227.23, 227.21, 227.28, 458.1, 461.2, 226; 350/96.29, 96.33

[56] References Cited

U.S. PATENT DOCUMENTS

| | | | |
|---|---|---|---|
| 4,792,689 | 12/1988 | Peterson | 250/227.23 |
| 4,924,870 | 5/1990 | Wlodarczyk et al. | 128/667 |
| 4,945,171 | 7/1990 | Haughland et al. | 549/224 |
| 4,954,435 | 9/1990 | Krauth | 356/320 |

FOREIGN PATENT DOCUMENTS

WO12232  12/1989  World Int. Prop. O. ......... 436/546

OTHER PUBLICATIONS

Goswami, K.; Kennedy, J. A.; Dandge, D. K.; Klainer, S. M.; "A Fiber Optic Chemical Sensor for Carbon Dioxide Dissolved in Sea Water", SPIE, vol. 1172, Chemical, Biochemical, and Environmental Sensors, 1989, pp. 225-232.

Primary Examiner—David L. Lacey
Assistant Examiner—Thomas E. Daley
Attorney, Agent, or Firm—Henry P. Sartorio

[57] ABSTRACT

A chemical sensor, such as a fiber optic chemical sensor, is self-calibrated by measuring two output values which behave differently in response to an analyte, and forming a ratio between the two measured output values to cancel out effects of variations in external factors such as temperature variations, differences between coatings, light (illuminator) variations, fouling, bleaching, leaching or the like. An indicator material may be used which produces both fluorescence and phosphorescence, both monomer and aggregate emission or absorption bands, emission or absorption bands with or without an isosbestic point, emission peaks at one wavelength at two different excitation bands, or emission peaks at two wavelengths for excitation at two wavelengths.

6 Claims, 7 Drawing Sheets

METHOD OF SELF-COMPENSATING A FIBER OPTIC CHEMICAL SENSOR

BACKGROUND OF THE INVENTION

The invention relates generally to fiber optical chemical sensors (FOCS) and other chemical sensors and more particularly to the elimination of sensor measurement errors caused by instrumental fluctuations, variations in optical properties, changes in temperature and slow loss of sensing material due to leaching or bleaching.

A fiber optic transmits light by total internal reflection at the core/clad interface when the refractive index of the clad is less than the index of the core. Optical fibers have been used in a wide variety of sensors, known as "optrodes" or "fiber optic chemical sensors" (FOCS), which can detect various chemical species or physical parameters. Illustrative U.S. Pat. Nos. include 4,582,809 to Block, et al.; 4,321,057 to Buckles; 4,399,099 to Buckles; 4,682,895 to Costello; 4,600,310 to Cramp, et al.; 4,509,370 to Hirschfeld; 4,542,987 to Hirschfeld; 4,447,546 to Hirschfeld, et al.; 4,634,856 to Kirkham; 4,846,548 to Klainer; 4,892,383 to Klainer, et al.; 4,824,206 to Klainer, et al.; 4,913,519 to Klainer, et al.; 4,272,485 to Lübbers; 4,269,516 to Lübbers; 4,476,870 to Peterson, et al.; 4,200,110 to Petersen, et al. U.S. patent applications Ser. No. 503,463 now U.S. Pat. No. 5,059,790, to Klainer, et al.; Ser. No. 501,144, now U.S. Pat. No. 5,026,139, to Klainer, et al.; Ser. No. 501,146 to Klainer et al.; Ser. No. 004,339, abandoned, to Walt, et al. also illustrate fiber optic chemical sensors.

In addition to fiber optic type chemical sensors in which the fiber optic is used to transmit excitation and detector signals to and from the active sensor, other chemical sensors have been developed in which the fiber optic has been illuminated. In particular, U.S. patent application Ser. No. 544,681 to Klainer, et al. describes a class of reservoir type chemical sensors in which the source and detector are mounted within the cell body.

Typically an analyte specific reaction chemistry (e.g., an organic dye, transition metals, and their complexes or charge transfer complexes) is immobilized on the FOCS or placed in the chemical sensor cell body. The absorption or emission intensity is modulated as these indicator materials interact with the specific analytes, thus producing a detector signal which provides a measure of the analyte of interest. For example, $Ru(bpy)_3^{2+}$ (Rutheniumtrisbipyridyl) which fluoresces with a peak at 610 nm, when excited at 440 nm, exhibits oxygen sensitive luminescence. In the presence of oxygen, $Ru(bpy)_3^{2+}$ luminescence is quenched and this quenching depends on the concentration of oxygen.

However, FOCS and other chemical sensors often exhibit poor performance because of degradation or other variations of the sensor. Sensor problems generally result from temperature variations, differences between coatings, light (illuminator) intensity changes and flicker, loss of indicator material and fouling of the sensor. For fluorescent sensors a particular problem is bleaching of the dye. Any of these variations, or others of a similar nature, cause changes in the sensor output which do not depend on the analyte, and thus produce an inaccurate measurement. For example, with reference to the oxygen sensor described above, if the $Ru(bpy)_3^{2+}$ undergoes degradation, or even if some $Ru(bpy)_3^{2+}$ leaks out of the sensor, then the emission intensity of $Ru(bpy)_3^{2+}$ will decrease, producing an erroneous oxygen reading. Thus it would be highly advantageous to have a FOCS or other chemical sensor in which the output is solely a function of the analyte or parameter of interest, and in which other variations in the sensor are compensated for so that they do not affect the sensor output. In particular, the objective is to use the FOCS or other sensor itself to provide the input for the necessary corrections.

SUMMARY OF THE INVENTION

Accordingly it is an object of the invention to provide a self-compensating FOCS or other chemical sensor.

It is also an object of the invention to provide a FOCS or other chemical sensor in which the output is solely a function of the analyte or parameter of interest, and in which other variations in the sensor are compensated for so that they do not affect sensor output.

It is another object of the invention to provide a FOCS or other chemical sensor which is not affected by temperature variations, differences between coatings, light (illuminator) variations, fouling, bleaching, leaching or the like.

It is a further object of the invention to provide a FOCS or other chemical sensor which is independent of sensor or indicator variations.

The invention is a self-compensating or internally calibrated FOCS or other chemical sensor, and the methodology for self-compensating or internally calibrating a FOCS or other chemical sensor. The invention is based on using two different spectral values from a single sensing reagent, and forming a ratio of the two measurements which removes variations in the output caused by the sensor. There are several possible embodiments, whereby, the ratiometric techniques can be used for sensor measurements:

a. The sensing reagent produces both fluorescence and phosphorescence emissions, only one of which is analyte specific.

b. At higher concentrations, the sensing reagent shows monomer and "aggregate" emission (or absorption) bands and these two bands have different quenching rates for a given analyte.

c. The interaction of an analyte makes two (or more) distinct absorption bands or emission bands with one or more clearly defined isosbestic points. One of the isosbestic points is considered as the reference and its constant intensity is ratioed with the variable intensity of a growing or decaying peak. Alternatively, the absorbance or the emission intensities of the two maxima can be ratioed, as in the next embodiment.

d. Interaction of an analyte results in two absorption or emission bands without isosbestic points. The peak intensities will be ratioed to obtain maximum stability with respect to calibration.

e. For a given emission wavelength, two excitation regions will develop because of the interaction of an analyte with the sensing reagents. The emission peak intensities in the two excitation bands will be ratioed.

f. A dye is excited at two different wavelengths, the emission intensities are measured and the two intensities are ratioed. This is applicable when the quantum yields of emission depend on wavelength.

DETAILED DESCRIPTION OF THE PREFERRED EMBODIMENTS

FIGS. 1A-D show a variety of sensor designs. The invention applies to any of these sensor designs or to other sensor designs which fall within the purview of fiber optic chemical sensors and non-fiber optic chemical sensors, such as reservoir cell sensors with either internal or external sources and detectors.

Figure 1A:
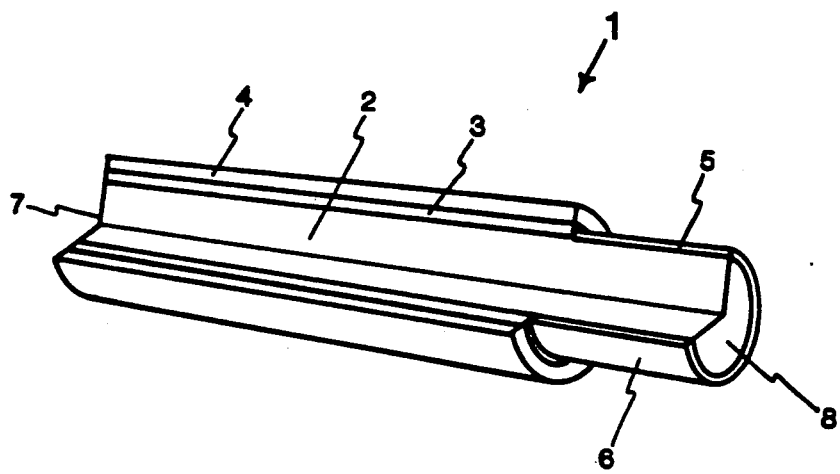
FIGS. 1 A,B,C,D are schematic views of 3 types of FOCS and one type of non-fiber optic sensor which may be made self-compensating sensors.

FIG. 1A shows side-coated FOCS 1. FOCS 1 is made of a fiber with core 2, clad 3 (with refractive index less than the refractive index of core 2) surrounding core 2, and (optional) buffer (protective layer) 4 surrounding clad 3. A portion 5 of the fiber is reduced to a bare core (core 2 with clad 3 and buffer 4 removed), and side-coating 6 is applied to core 2 along exposed portion 5. Side-coating 6 is the reactive coating. The light enters FOCS 1 at end 7. End 8 is the distal end (termination of FOCS 1).

Figure 1B:
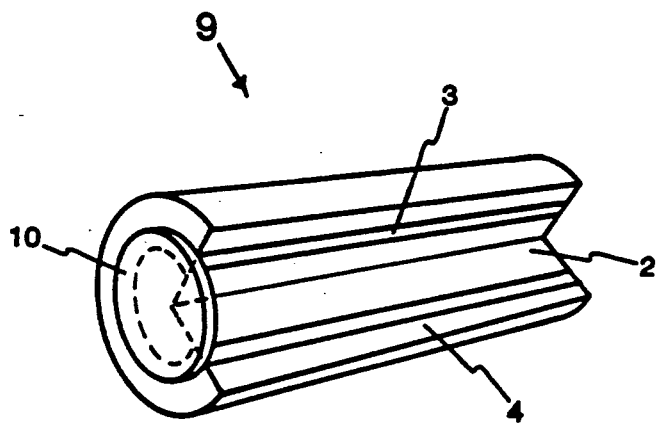

FIG. 1B shows tip-coated FOCS 9. FOCS 9 is made of core 2, surrounding clad 3, (optional) buffer 4 around clad 3, and tip-coating 10. Tip-coating 10 can be the same material as side-coating 6.

Figure 1C:
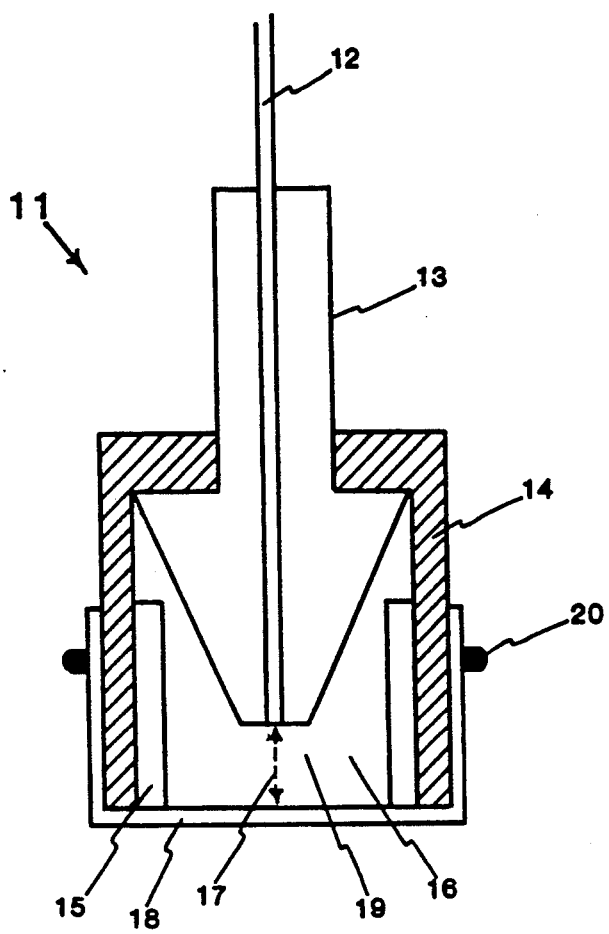

FIG. 1C shows a reservoir FOCS 11. Fiber optic 12 is held in fiber optic mount 13 which is placed in reservoir cell body 14. Spacers 15 control volume 16 and optical path 17 of cell body 14. Membrane 18 holds sensing solution 19 in cell body 14. Retaining ring 20 makes membrane 18 liquid tight. Sensing solution 19 may be a solution of the same material as side-coating 6 and/or tip coating 10.

Figure 1D:
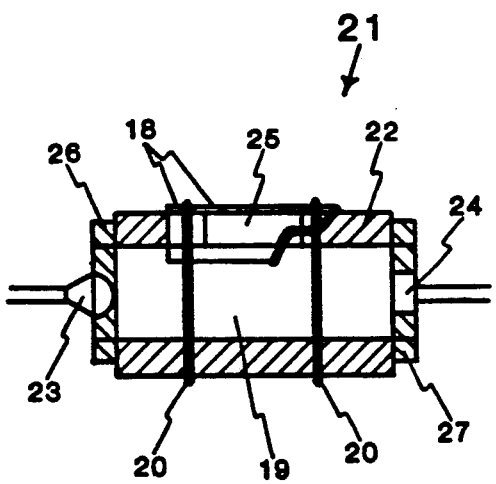

FIG. 1D shows a reservoir chemical sensor 21 which does not utilize optical fibers. Sensor 21 is formed of a cell body 22 having a port 25 formed therein. Port 25 is covered by a semi-permeable membrane 18 which is held in place by retaining rings 20. A source 23 and a detector 24 are mounted in opposed ends of cell body 22, by attachment means or adapters 26, 27, respectively. Sensor 21 is filled with sensing solution 19.

In FOCS 1, 9 and 11, and sensor 21, light enters the sensor and excites the sensing chemistry (6, 10 and 19) which then interacts with the target (chemical/biological) of interest. This interaction results in a spectral change (intensity, wavelength shift, change of lifetime) which can supply both qualitative and quantitative information about the sample being measured.

Figure 2:
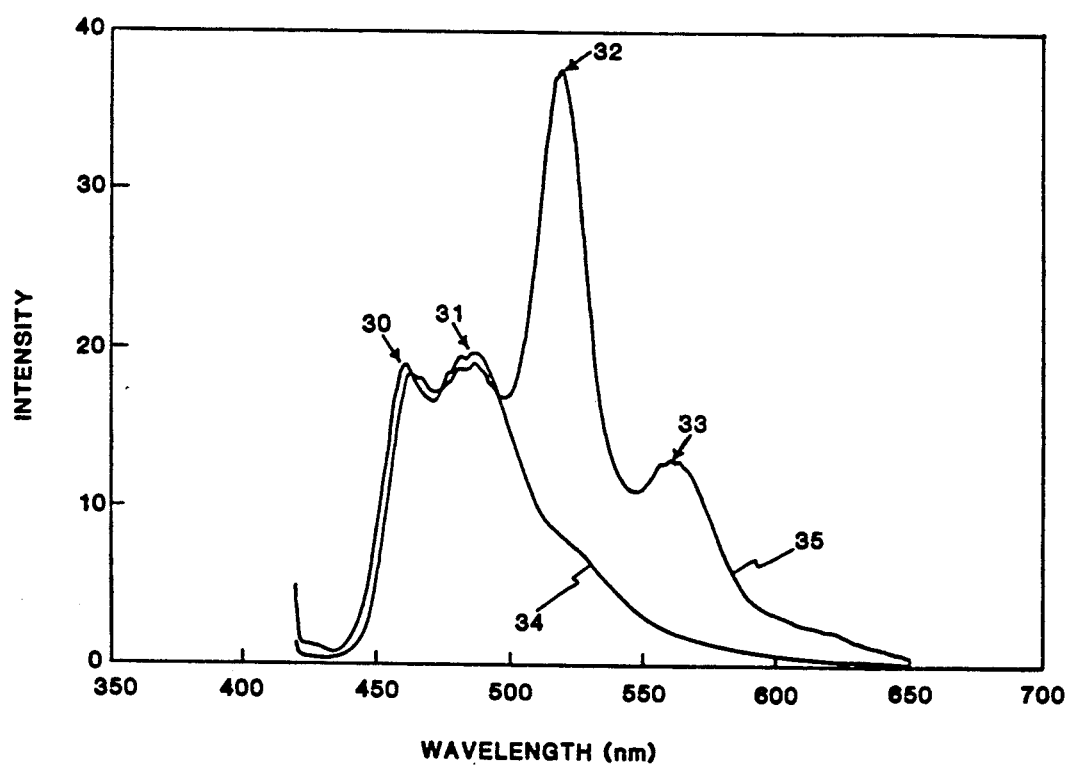
FIG. 2 is a graph of intensity vs. wavelength showing separate fluorescence and phosphorescence emissions of an indicator material, biacetyl, in the presence and absence of oxygen.

In a preferred embodiment of the invention, as shown in FIG. 2, the indicator material of the sensor is a dye which produces both fluorescence and phosphorescence emissions, only one of which is analyte specific. Any luminescent species having analyte specific fluorescence and nonspecific phosphorescence or vice versa can be used. An example is biacetyl luminescence quenching by oxygen. Biacetyl (or Diacetyl or 2,3-Butanedione) has fluorescence peaks 30, 31 at 450 nm and 490 nm and phosphorescence peaks 32, 33 at 518 nm and 570 nm with corresponding excitation at 420 nm. The phosphorescence peaks at 518 and 570 nm are very sensitive to oxygen while the fluorescence peaks at 450 and 490 nm are oxygen insensitive. Emission spectra curve 34 of biacetyl (in cyclohexane solution) is produced in the presence of 20% oxygen while emission spectra curve 35 is produced in the absence of oxygen. Therefore, by ratioing the peak intensities of any of the phosphorescence peaks to any of the fluorescence peaks, a measurement signal is obtained which is independent of bleaching, leaching, degradation, temperature and other external factors. This is because the non-specific peak reacts to all the external factors, while the specific peak responds to both the external factors as well as the analyte of interest. By forming a ratio the effect of the external factors is compensated so that the variations in the fluorescence to phosphorescence ratio are due only to the analyte (external effects X oxygen effect/external effects=oxygen effect). Thus one of the luminescence peaks acts as an internal standard. The technique can be applied to pH, $CO_2$ and other sensors as well as $O_2$.

Figure 3:
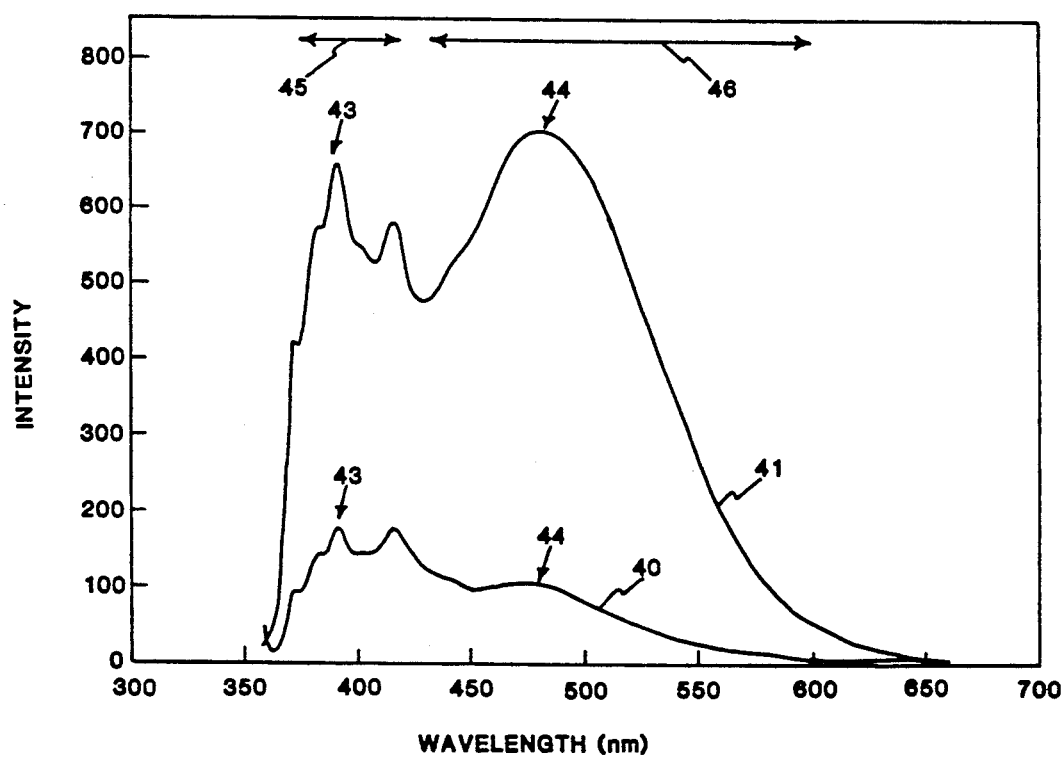
FIG. 3 illustrates the "monomer" and "aggregate" emission method using pyrene, in the presence and absence of oxygen.

In the second embodiment, shown in FIG. 3, the sensing dye exhibits two emission (or absorption) bands depending on the concentration of the sensing dye or on the concentration of a non-sensing entity (e.g., a polymer). These two bands have different rates of quenching toward a particular analyte. The intensities at the peak wavelengths are ratioed. For example, when a $10^{-3}$M solution of pyrene in toluene is excited in the ultraviolet, two emissions appear as shown in the emission spectra curve 40, at 20% oxygen concentration, and emission spectra curve 41 with no oxygen present. The peaks in the 360-420 nm region (band 45) belong to the monomer emission, whereas, the 440-640 nm band (band 46) is the excited dimer or excimer band. As FIG. 3 shows, in the presence of 20% oxygen (emission spectra curve 40), the excimer band decreases more than the monomer band. Ratioing the intensities at 390 nm (peak 43) and 480 nm (peak 44), at any oxygen concentration, gives sensor performance which is independent of many variables which affect FOCS performance.

Figure 4:
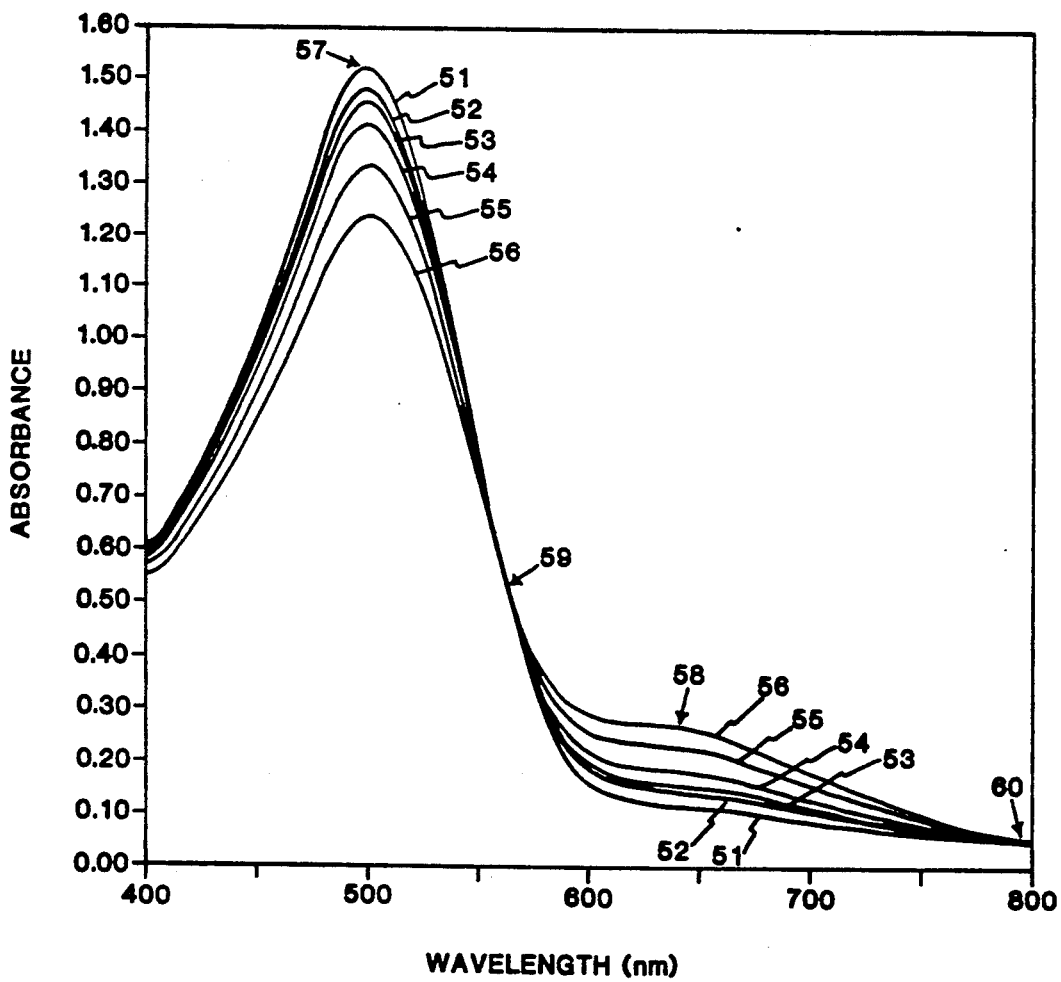
FIG. 4 illustrates the isosbestic point method, and also the two absorption band method, using congo red in the presence of chlorine.

In certain situations, the interaction of an analyte with the sensing reagent leads to growth of a new absorption or emission band with the simultaneous decay of the original band. The existence of two distinct species is indicated by the appearance of clearly defined isosbestic points. In a third embodiment, an isosbestic point is used as the internal standard. FIG. 4 shows the interaction of congo red with chlorine. Absorption spectra curves 51, 52, 53, 54, 55, 56 of congo red and its complex with chlorine result from no chlorine, and 50, 100, 200, 400 and 800 ppb chlorine, respectively. Congo red shows an intense absorption band in the visible wavelength range with a peak 57 at 500 nm. As chlorine is added, the absorbance at 500 nm diminishes while another absorption band grows with peak 58 at 650 nm. As FIG. 4 shows, the absorbance at 560 nm and 800 nm remains unchanged. These are called the isosbestic points (59, 60, respectively). For an accurate determination of chlorine, the absorbances at 500 nm and 560 nm, or 650 nm and 560 nm are ratioed. The isosbestic point at 800 nm can also be used. The choice of 560 nm is more accurate because detector response at 500 nm or 650 nm is much closer to 560 nm. The absorbances at 560 nm and 800 nm will change only because of external effects. At 500 nm and 650 nm the absorbances are affected equally by the external effects as well as the presence of chlorine. The ratio is, therefore, only sensitive to chlorine concentration.

When the interaction of an analyte produces two absorption or emission bands without an isosbestic point, or alternatively even when there is an isosbestic point, the intensities of the two maxima can be ratioed. This is illustrated using peaks 57, 58 in FIG. 4, which can be ratioed. This fourth embodiment is similar to that shown in FIG. 3.

Figure 5:
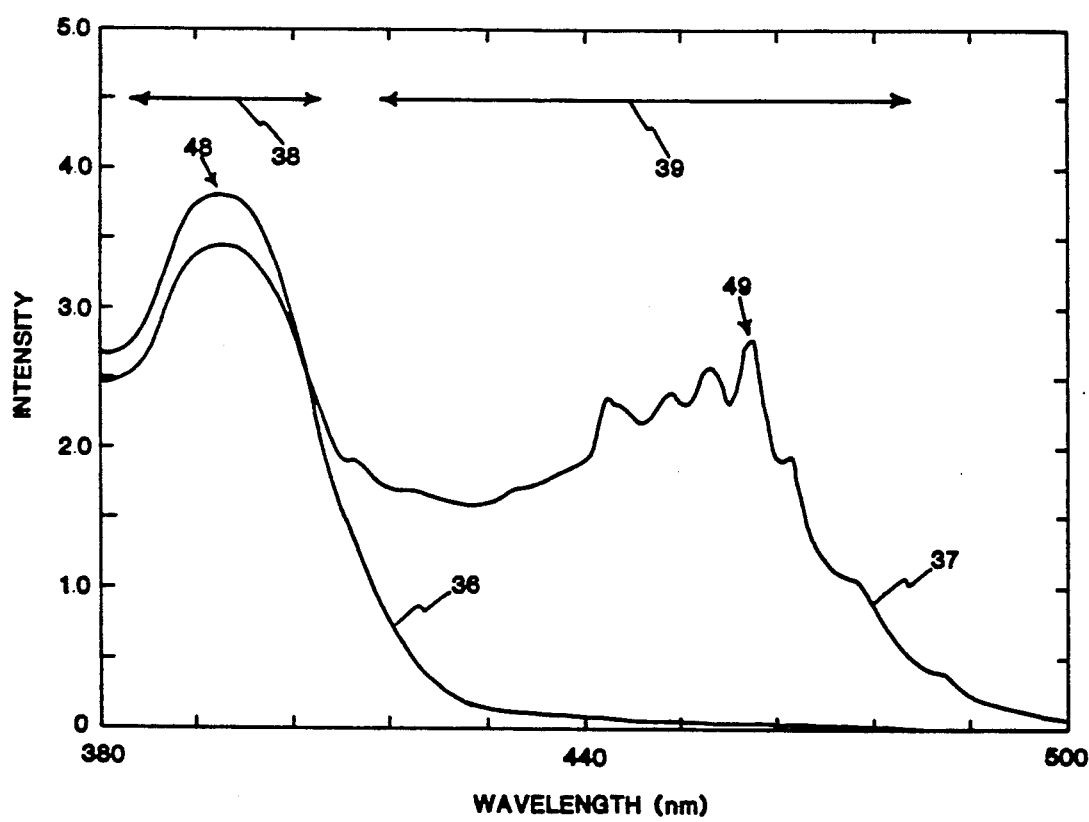
FIG. 5 illustrates the two excitation/single emission method, using hydroxypyrenetrisulfonate as a function of pH.

In a fifth embodiment, shown in FIG. 5, the emission spectra of the sensor material provides two different excitation bands or regions which behave differently as a function of the analyte. Emission spectra curves 36, 37 for hydroxypyrenetrisulfonate (HPTS) at a pH of 5.0 and 7.0, respectively, (pH=hydrogen ion concentration) are shown in FIG. 5. The curves 36, 37 are plots of the emission intensity of HPTS at 570 nm as a function of the excitation wavelength over the range 380-500 nm. The emission spectra has two distinct excitation regions or bands, a first region 38 between 380-410 nm and a second region 39 between 420-480 nm, which behave very differently as a function of pH. Region 38 varies only slightly in emission intensity as a function of pH while region 39 varies greatly. Thus, the sensor can be self-calibrated by taking a ratio of intensity peaks 48, 49 within the two excitation bands 38,39, respectively.

Figure 6:
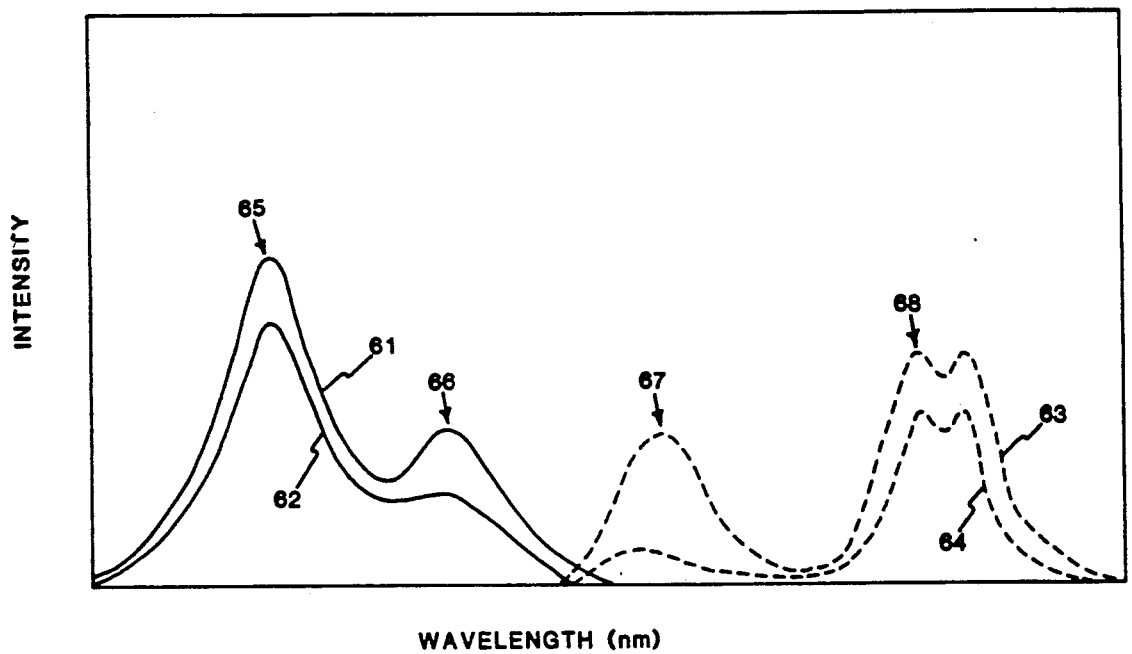
FIG. 6 illustrates the two excitation/two emission method, using a mixture of crystal violet and polyacrylic acid as a function of pH.

In a sixth embodiment, shown in FIG. 6, the sensor material is excited at two different wavelengths and the emission intensities produced by the two excitations behave differently as a function of the analyte. Self-compensation is performed by ratioing the peak emission intensities at the two excitation wavelengths. FIG. 6 shows both the absorption and emission spectra of crystal violet with polyacrylic acid (in water solution) as a function of pH. Curves 61,62 are the absorption spectra at a pH of 4.0 and 7.5, respectively. Curves 63, 64 are the corresponding emission spectra at a pH of 4.0 and 7.5, respectively. The absorption spectra has peak 65 at 508 nm and peak 66 at 590 nm while the emission spectra has a peak 67 at 635 nm and a peak 68 at 740 nm. Excitation of 508 nm leads to emission at 740 nm while excitation at 590 nm leads to emission at 635 nm. It is the combination of crystal violet with polyacrylic acid which produces the double peak; crystal violet alone provides the 590/635 nm peak while the combination adds the 508/740 nm peak. Peak 67 behaves differently from peak 68 as a function of pH, i.e., it changes more, as shown in FIG. 6. Therefore, a self-calibrated or compensated sensor output signal is produced by ratioing peaks 67, 68.

The above mentioned examples illustrate how ratioing is used for self-compensating FOCS and other chemical sensor measurements. The corrections are intrinsic to the spectral response of the sensing chemistry. The self-correction is based on comparing signal intensities at two different wavelengths where the two signal intensities are affected in a different functional manner by the presence of the analyte. Since both signal values will be affected in the same way by the external factors, a ratio of the two signal values will cancel out the variation introduced by the external factors. The two wavelengths can be either input or output wavelengths; i.e., the output signal (e.g., emission or absorption spectra) is measured at two different wavelengths or is measured at a single wavelength for two different excitation wavelengths. The two compared signals must behave differently with respect to the analyte, e.g. only one changes, or one increases while the other decreases, or they change by different relative amounts. For example, a signal that varies only slightly or not at all with the species of interest is ratioed with a signal that varies with the species of interest; both vary with the external factors whose effect is cancelled out. The resultant signal is only a function of the analyte. Thus, the invention requires a minimum of two distinct differently varying spectral features in response to an analyte.

Figure 7:
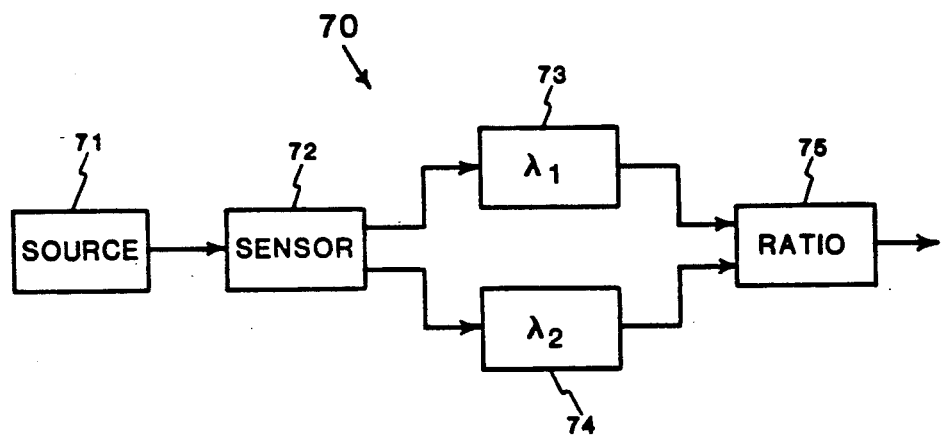
FIG. 7 is a schematic view of a self-calibrating sensor apparatus.

FIG. 7 is a schematic view of a self-compensating sensor apparatus 70. Source (excitation means) 71 provides an input signal into sensor 72. Sensor 72 may be any of the types illustrated in FIGS. 1A-D, or any other type chemical sensor in which an optical signal is produced which has the requisite two distinct differently varying spectral features in response to a species of interest. Sensor 72 may produce any of the effects shown in FIGS. 2-6, or other similar effects. The output of sensor 72 is measured at each of two wavelengths, as previously described, by measurement means 73, 74, respectively (which may be combined in a single physical unit). The measured signals at the two wavelengths are input into ratio-forming means 75, which provides a self-calibrated output signal. Ratio-forming means 75 may be a computer or other calculating means to provide a self-calibrated output (and may be used for further signal processing in addition to forming the ratio of the two signals). Source 71 may provide excitation at a single wavelength or at two (or more) wavelengths and the measurement of the sensor output at the two wavelengths may be made substantially simultaneously or sequentially.

Changes and modifications in the specifically described embodiments can be carried out without departing from the scope of the invention which is intended to be limited only by the scope of the appended claims.

We claim:

1. A method of self-compensating a chemical sensor for variations in external factors when detecting oxygen, comprising:
    forming the sensor with an indicator material of biacetyl which produces both fluorescence emissions at 450 nm and 490 nm and phosphorescence emissions at 518 nm and 570 nm, only the phosphorescence emissions of which are analyte specific;
    exciting the indicator material at 420 nm to produce fluorescence and phosphorescence peaks at said wavelengths;
    forming a ratio of a fluorescence peak intensity at 450 nm or 490 nm to a phosphorescence peak intensity at 518 nm or 570 nm;
    determining oxygen changes from the ratio.

2. A method of self-compensating a chemical sensor for variations in external factors when detecting pH, comprising:
    forming the sensor of an indicator material of a mixture of crystal violet and polyacrylic acid which is excitable at a first wavelength of 508 nm and second wavelength of 590 nm;

exciting the indicator material at the first and second wavelengths;

measuring emission intensity peaks of the indicator material at 635 nm and 740 nm when excited at the first and second wavelength;

forming a ratio of the emission intensity peaks at 635 nm and 740 nm when excited at the first and second wavelength;

determining pH changes from the ratio.

3. A method of self-compensating a chemical sensor for variations in external factors when detecting chlorine, comprising:

forming the sensor with an indicator material of congo red which produces an absorption spectra which has an isosbestic point at 560 nm and at 800 nm and absorption peaks at 500 nm and 650 nm;

exciting the indicator material to produce the absorption spectra;

forming a ratio of a peak intensity of the absorption spectra at 500 nm or 650 nm to the intensity at the isosbestic point at 560 nm or 800 nm;

determining chlorine changes from the ratio.

4. A method of self-compensating a chemical sensor for variations in external factors when detecting oxygen, comprising:

forming the sensor with an indicator material of a solution of pyrene in toluene which produces both a monomer emission band between 360–420 nm and an aggregate emission band between 440–640 nm which have different quenching rates for oxygen;

exciting the indicator material to produce the monomer and aggregate bands;

forming a ratio of a monomer band peak intensity at 390 nm to an aggregate band peak intensity at 480 nm;

determining oxygen changes from the ratio.

5. The method of claim 4 comprising forming the indicator material of a $10^{-3}$M solution of pyrene in toluene.

6. A method of self-compensating a chemical sensor for variations in external factors when detecting pH comprising:

forming the sensor of an indicator material of hydroxypyrenetrisulfonate which produces an emission intensity at a single wavelength of 570 nm which has a first peak in a first excitation band between 380–410 nm and a second peak in a second excitation band between 420–480 nm;

exciting the indicator material at the first and second excitation bands;

measuring emission intensity peaks at 570 nm when excited at the first and second excitation bands;

forming a ratio of the emission intensity peaks at 570 nm when excited at the first and second excitation bands;

determining pH changes from the ratio.

* * * * *